US008690772B2

(12) United States Patent
Hately et al.

(10) Patent No.: US 8,690,772 B2
(45) Date of Patent: Apr. 8, 2014

(54) ACTIVATION AND CONTROL DEVICE FOR COUPLING TWO MUTUALLY ACTIVATABLE AUTOMATIC INTERVENTION SYSTEMS

(75) Inventors: Paul Alastair Hately, Portsmouth (GB); Mark Johnson, Milton Keynes (GB); Jerry Brown, Essex (GB)

(73) Assignee: Swiss Reinsurance Company Ltd., Zurich (CH)

( * ) Notice: Subject to any disclaimer, the term of this patent is extended or adjusted under 35 U.S.C. 154(b) by 819 days.

(21) Appl. No.: 12/095,649

(22) PCT Filed: Nov. 28, 2006

(86) PCT No.: PCT/EP2006/068982
§ 371 (c)(1),
(2), (4) Date: Dec. 2, 2008

(87) PCT Pub. No.: WO2007/063057
PCT Pub. Date: Jun. 7, 2007

(65) Prior Publication Data
US 2010/0179451 A1  Jul. 15, 2010

(30) Foreign Application Priority Data

Nov. 30, 2005  (WO) .................. PCT/EP2005/012770

(51) Int. Cl.
*A61B 5/00* (2006.01)
*A61B 5/103* (2006.01)
*A61B 5/117* (2006.01)

(52) U.S. Cl.
USPC ............ 600/301; 600/300; 600/587; 600/595

(58) Field of Classification Search
USPC ................................ 600/587, 595, 300, 301
See application file for complete search history.

(56) References Cited

U.S. PATENT DOCUMENTS

| 5,235,507 | A | * | 8/1993 | Sackler et al. | 705/2 |
| 2001/0032099 | A1 | * | 10/2001 | Joao | 705/2 |
| 2003/0229514 | A2 | | 12/2003 | Brown | |
| 2004/0078219 | A1 | | 4/2004 | Kaylor et al. | |
| 2004/0078228 | A1 | * | 4/2004 | Fitzgerald et al. | 705/2 |
| 2004/0236187 | A1 | | 11/2004 | Bock et al. | |
| 2005/0113721 | A1 | * | 5/2005 | Reed et al. | 600/595 |
| 2006/0241521 | A1 | * | 10/2006 | Cohen | 600/595 |

FOREIGN PATENT DOCUMENTS

WO  01 97686  12/2001

* cited by examiner

Primary Examiner — Max Hindenburg
Assistant Examiner — Adam Eiseman
(74) Attorney, Agent, or Firm — Oblon, Spivak, McClelland, Maier & Neustadt, L.L.P.

(57) ABSTRACT

Activation and control apparatus (11) and also appropriate process for coupling two reciprocally activatable automated intervention systems (10/12) for coverage events in medical diagnosis and/or therapy processes, where the activation and control apparatus (11) comprises a proxy trigger (14), which proxy trigger (14) comprises at least first measuring apparatuses (141) which can be used to detect first measurement parameters on the basis of user-specific walking distance and/or a user-specific visual accuracy and/or a user-specific sitting period, and/or second measuring apparatuses which can be used to detect second measurement parameters on the basis of user-specific communication ability. The measurement parameters can be stored in a lookup table (15) in association. The proxy trigger (14) also comprises a filter module (146), where the filter module (146) can be used to generate appropriate activation parameters on the basis of the measurement parameters in the lookup table (15) and associated, synchronized threshold parameters if at least one of the measurement parameters exceeds the associated threshold value. In addition, the activation and control apparatus (11) also comprises means (13) for generating the activation data on the basis of the activation parameters.

41 Claims, 3 Drawing Sheets

ACTIVATION AND CONTROL DEVICE FOR COUPLING TWO MUTUALLY ACTIVATABLE AUTOMATIC INTERVENTION SYSTEMS

FIELD

The invention relates to an activation and control apparatus for coupling two reciprocally or complementarily activatable automated intervention systems, where the automated intervention systems comprise a multiplicity of associated users and where the automated intervention systems are activated using activation data from the activation and control apparatus. In particular, the invention relates to an activation and control apparatus for coupling automated intervention systems for coverage events in medical diagnosis and/or therapy processes.

BACKGROUND

These deep-seated changes in the age structure of the population have developed in recent decades and will continue to develop in the coming decades. These demographic changes are simultaneously accompanied by vast development in the available technology for diagnosis and therapy systems. The effects of these changes would result in collapse of the conventional intervention systems or coverage systems in this area in practice, particularly in the cash-value-based intervention systems for covering intervention events in medical diagnosis and/or therapy processes, especially as far as their financeability is concerned. Today, every fifth citizen is above 60 years old; in 2030, this will be every third one. The number of people above 80 years old is rising continuously; their number will increase by almost 90 percent by the year 2030. At the same time, the total population will fall by 10 percent by the year 2030. All intervention or coverage systems in the health sector will have to deal with this trend: both apportionment systems, in which all of the costs need to be financed totally from the ongoing income from premiums, and prospective entitlement coverage systems, for which the calculation of premiums also takes account of the use of health services, which increases with age. By way of example, private health insurance systems typically use the prospective entitlement coverage process for calculation. The basis of these systems is that even now they form the provision for future damage events. The stored financial collateralization levels formed in this way determine the survival of the system, in the expected situation, where an ever greater number of elderly people in retirement oppose an ever smaller number of people of working age. These systems should, in principle, not prompt the premiums to be transferred to other generations. In terms of insurance, every age group raises the cost of illness for its age group. Older insured parties are therefore, in principle, not dependent on the ability of the younger generation to pay. What are known as ageing provisions should therefore cover these insured parties for the future.

If the aforementioned intervention systems are used as single apparatuses under the prerequisite of complete intervention or complete or as complete as possible coverage of all possibilities, they have been found to be too vulnerable and unstable. For each of these intervention systems, framework parameters are therefore normally determined today, or the stipulated limits for intervention within which the intervention system can be activated for a specific case are synchronized with other systems. In the prior art, it is already the practice to introduce multistage intervention systems in order to get around this problem. These systems frequently comprise, by way of example, a first (public and/or private) stage with first intervention systems and at least one second stage with second intervention systems for direct intervention and/or cash-value-based coverage of events which the first stage does not cover or covers only partially by means of activation. The first and second stages typically involve different systems which are independent of one another. One drawback of this prior art is that the various stages cannot be clearly chained to one another for a wide variety of reasons, inter alia because the stages need to work independently of one another. Another drawback is that these systems have to date hardly been able to be automated, or have been able to be automated only with difficulty and at great cost, with the prior art. In addition, all of these systems were usually too unstable and vulnerable to error for effective use, despite their coupling. Another drawback was that all of these systems always only worked locally, i.e. in specific countries, since the technical structure of the health and insurance service usually differs considerably from country to country. It is an intrinsic property of these unautomated or semi-automated systems from the prior art that they always remain static, which prevents dynamic adaptation (self-adapting) of the systems. The technical basis for effective intervention or compensation is secure registering, rapid association and checking of the instances of damage which have occurred. In the case of cash-value-based intervention apparatuses, not only the damage sum as such but also more and more instances of intervention or instances of damage are frequently accompanied by an unclear legal situation from laborious and costly court proceedings. Particularly in the case of very costly diagnosis and/or therapy processes which are needed quickly, this can result in a financial disaster for the user or the insured party.

Systems for handling damage events in medical and/or therapeutic processes are known in the prior art. The international patent specification WO 02/077764 describes a process for automating such payments for services. Equally, partially automated intervention systems are known in the prior art. The patent specification US 2002/0172313 in the prior art describes a cash-value-based intervention system for medical and/or therapeutic processes. User data or patient data are transmitted to the intervention system and are filtered as appropriate. Finally, real-time or approximately real-time intervention systems and coverage systems are also known in the prior art and can be used to transmit and manage data securely between the service provider and the cash-value-based intervention system. The international patent specification WO 02/086688 in the prior art describes such a system. Equally, the international patent application PCT/US00/21529 (CA2381253) from the company ACE INA Holding, INC, Philadelphia, (US), shows an operational intervention system, where cash-sum values are transmitted and operational intervention is activated in response when a determinable and detectable event occurs. In all of the systems from the prior art, however, complete automation of the process is not possible. In particular, they relate almost exclusively to intervention systems from the first stage. Similarly, dynamic adaptation, e.g. concerning country-specific peculiarities and/or changes in the medical and/or therapeutic processes over time, is not an effective and simple matter with any system from the prior art. However, another important problem of all of these systems is also that the seamless coupling or reciprocal activation in multistage intervention systems not only produces problems but also evades automation almost completely. In this context, seamless means not only rapid and efficient activation of the intervention systems from the second stage if the intervention systems from the first stage cannot be activated, but also that effectively all possible intervention events are covered by at least one of the intervention systems. Another drawback to be mentioned is the country-specific foibles, for which such intervention systems can usually be implemented only with great technical complexity, particularly as far as the seamless coupling of the systems is concerned.

SUMMARY

It is an object of this invention to propose a system and an appropriate process for an activation and control apparatus for coupling two reciprocally or complementarily activatable automated intervention systems which do not have the aforementioned drawbacks. In particular, it is intended to relate to automated intervention systems for coverage events in medical diagnosis and/or therapy processes. There are also meant to be solutions which allow such control and/or operational intervention systems to be automated without any loss of stability to the systems. At the same time, the system is intended to have the aforementioned advantages of speed and time savings etc. as a result of the automation. The apparatus and/or the overall system are also meant to be able to be adapted to country-specific characteristics simply and inexpensively. Quite generally, the system is intended to be able to adapt itself automatically and/or dynamically to changed conditions. The intention is also solutions which handle intervention events in real time and are able to generate and transmit the appropriate activation impulses or are able to initiate activation. In this context, the two stages are meant to mesh seamlessly, so that all events are securely registered by at least one stage.

In line with the present invention, this aim is achieved particularly by the elements of the independent claims. In addition, further advantageous embodiments can be found in the dependent claims and the description.

In particular, the invention achieves these aims by virtue of an activation and control apparatus being used to couple two reciprocally or complementarily activatable automated intervention systems for coverage events in medical diagnosis and/or therapy processes, where the automated intervention systems comprise a multiplicity of associated users and can be activated by means of activation data from the activation and control apparatus, by virtue of the activation and control apparatus comprising a proxy trigger, which proxy trigger comprises first measuring apparatuses and/or registering apparatuses, where the first measuring apparatuses can be used to detect first measurement parameters on the basis of user-specific walking distance and/or a user-specific visual accuracy and/or a user-specific sitting period, and to store them in a lookup table in association with the user, and/or by virtue of the proxy trigger comprising second measuring apparatuses and/or registering apparatuses, where the second measuring apparatuses can be used to detect second measurement parameters on the basis of user-specific communication ability, and to store them in a lookup table in association with the user and where the user-specific communication ability comprises at least aural and/or visual and/or comprehension measurement parameters for the user, and/or by virtue of the proxy trigger comprising third measuring apparatuses and/or registering apparatuses, where the third measuring apparatuses can be used to detect third measurement parameters on the basis of the user-specific ability to drive a motor vehicle, and to store them in a lookup table in association with the user, and/or by virtue of the proxy trigger comprising fourth measuring apparatuses and/or registering apparatuses, where the fourth measuring apparatuses can be used to detect fourth measurement parameters on the basis of the user-specific ability to lift oneself or stand independently, and to store them in a lookup table in association with the user, and/or by virtue of the proxy trigger comprising fifth measuring apparatuses and/or registering apparatuses, where the fifth measuring apparatuses can be used to detect fifth measurement parameters on the basis of the user-specific ability to write and/or to use a keypad-based input apparatus, and to store them in a lookup table in association with the user, by virtue of the proxy trigger comprising a filter module, where the filter module can be used to generate appropriate activation parameters on the basis of the measurement parameters in the lookup table and associated, synchronized threshold parameters, and to transmit them to the activation and the control apparatus if at least one of the measurement parameters exceeds the associated threshold value, and by virtue of the activation and control apparatus comprising means for generating the activation data on the basis of the activation parameters. At least one of the measuring apparatuses can comprise a definable time-based threshold value. The time-based threshold value can be used to stipulate the period of a measurement, for example. The first and/or fourth measuring apparatuses may comprise at least one eyetracking apparatus and/or one or more pressure sensors, for example. The second measuring apparatuses may comprise apparatuses for generating different multimedia data and/or audio output apparatuses and/or image presentation apparatuses and touchscreens and/or appropriate input appliances, for example. The third measuring apparatuses may comprise means for bidirectionally accessing appropriate databases with data concerning the health-related framework parameter for motor vehicle driver licensing, for example. The third measuring apparatuses may additionally comprise means for access-controlled and/or encrypted access to medical and/or national databases with data concerning the vehicle driver licensing for one or more users, for example. The fifth measuring apparatuses may comprise at least input apparatuses with keypad-based input elements and/or pressure-sensitive input tablets and/or touchscreens, for example. One advantage of the invention is, inter alia, that coverage events which are not registered by the first intervention system can automatically be registered by the second intervention system, and appropriate activation can be initiated. The intervention systems may comprise cash-value-based cash-value-based intervention systems for medical and/or therapeutic processes, for example. However, it is also possible for the intervention systems to be control and alarm apparatuses or systems for direct intervention with the user which are activated upon detection of appropriate events with the user. This can be done by coupled and/or graduated treatment interventions, for example, such as initiation of different metering for appropriate metering apparatuses, e.g. for automated administration of medicaments etc. Equally, intervention systems are possible which are activated, in the sense of alerted, by the activation apparatus, for example (e.g. automated emergency intervention by medically trained personnel or automated initiation of ambulance services etc. etc.). This has not been possible in the prior art to date. One of the reasons for the failure of the systems from the prior art is, inter alia, that the correlation of the control systems and hence also the activation operations were conventionally not able to be avoided, or could be avoided only with difficulty. Another drawback was the great complexity of the control processes, which also allowed automation only in part. By contrast, one of the advantages, inter alia, of the inventive system is that it can be implemented on a technical basis and is rapid and controllable as a result of its simple structure. In particular, the time involvement can be minimized by virtue of the automation, and instances which are otherwise difficult to detect can be detected reliably. Similarly, the speed of the inventive apparatus guarantees that coverage events are detected in good time and are also covered effectively by the intervention systems. The automation also allows a great saving on work involved for operating the intervention systems, which also makes the inventive activation and control apparatus inexpensive. As mentioned, the inventive apparatus allows full automation of such a coupled system, particularly from the second stage, the first time. Despite great efforts by industry and technology, this automation has been elusive to date. As mentioned, it is important for the user or the patient that the coverage event is adopted quickly and cleanly by the intervention system, since otherwise it can mean financial ruin for him. In many countries, health services can today be obtained only by prepaid processes. Usually, real emergency treatments are naturally an exception to this. Just as important as the system's reaction speed is that the apparatus based on the invention also minimizes the user involvement in handling the coverage event or eliminates it completely. In all known intervention systems from the prior art, a coverage event cannot be handled without a complicated feedback process with the user or service purchaser. Particularly what are known as pay guarantor systems (tiers payant/tiers garant), where the user is always the guarantor between the service provider and the intervention systems, may be typical examples of the aforementioned problems of the prior art. Particularly in the case of rare exceptional instances which are difficult to register, the systems require the cooperation of the user himself, otherwise they fail at this point. It is naturally clear that such failure of the intervention systems usually exclusively hits the user and/or the service provider (e.g. when the user is unable to pay as a result). In the extreme case, this can render entire health systems unstable. Ultimately, the system must be able to be adapted to specific countries more easily.

In one variant embodiment, the proxy trigger comprises means for dynamic user-specific registering of at least some of the threshold values. This variant embodiment has the advantage, inter alia, that the inventive apparatus or the entire coupled system can have a self-adaptive response to the environment.

In another variant embodiment, for the dynamic registering, for example, the proxy trigger may comprise means for detecting appropriate user-specific parameters, which user-specific parameters can be taken as a basis for dynamically adapting the threshold values. That is to say that the threshold values can therefore be adapted on a user-specific basis. This allows person-specific foibles to be considered independently and adapted individually by an intervention system for the first time. This results in a totally new type of operation and response by the system.

In another variant embodiment, the proxy trigger comprises a network module which can be used to access one or more databases of at least one medical or therapeutic service provider, and the proxy trigger comprises a second filter module for aggregating historical user data, at least one of the threshold values being able to be determined using the filter module on the basis of the aggregated historical data. This variant embodiment has the advantage, inter alia, that it allows accurate and, above all, complete automated adaptation of the threshold values. This has not been possible in the prior art to date.

In yet another variant embodiment, at least one of the threshold values is determined on the basis of cash-sum values associated with a service. This variant embodiment has the advantage, inter alia, that particularly in the case of cash-value-based intervention systems the operation of the systems can be controlled and maintained by the inventive activation and control apparatus. The associated cash-value sums can be adapted dynamically, in particular, e.g. on the basis of the network access to appropriate national and/or private databases, e.g. of medical and/or therapeutic service providers. The proxy trigger can comprise means for bidirectional and/or access-controlled and/or encrypted access to one or more databases of a medical and/or therapeutic service provider and/or national service control points, for example.

In one variant embodiment, the proxy trigger comprises a first supplementary trigger module, the first supplementary trigger module comprising a memory unit for storing definable triggerable illness type data and/or illness status data and/or treatment type data, and the first supplementary trigger module being able to be used by at least one medical service provider to filter data concerning services provided in diagnosis and therapy processes on the basis of the illness data types and/or illness status data and/or treatment type data, and detection of one of the illness type data and/or illness status data and/or treatment type data prompting the charging data with charging parameters for crediting cash-sum values to the patient and/or medical service provider to be able to be transmitted to a clearing module. By way of example, the stored data comprise data from historical and/or completed damage events for other patients and/or users of the system. This variant embodiment has the advantage, inter alia, that new treatment processes and therapy processes resulting in new, altered long-term dependencies for the affected patients are automatically registered correctly and retriggered by the system, for example. The illness type data and/or illness status data may comprise at least data concerning specific types of cancer and/or data concerning the cancer stage of a specific type of cancer, for example. The treatment type data may comprise at least data concerning specific organ transplants, for example. The treatment type data may comprise at least data concerning specific cardiac surgical intervention, for example. The illness type data may comprise at least data concerning illnesses with the expected long-term dependency of the user in question, for example. The supplementary trigger module may comprise means for dynamically registering the long-term dependency of different illness types based on locally stored data from medical service providers based on services provided in diagnosis and therapy processes, for example.

In another variant embodiment, the system comprises a second supplementary trigger module, which second supplementary trigger module comprises a registering unit for accessing one or more databases of least one medical service provided via a network, and where the second supplementary trigger module comprises a filter unit for aggregating provided historical service data, which second supplementary trigger module comprises an approximation module, with at least one storable time-based correlation parameter being able to be determined on the basis of the dependency between the aggregated historical service data and their time-based occurrence, and which second supplementary trigger module comprises a comparison module, which comparison module can be used to compare stored chronological correlation factors with a definable correlation threshold value, where exceeding the correlation threshold value prompts the second stage to be activated by means of the system and/or charging data with charging parameters for debiting cash-sum values to the patient and/or medical service provider to be transmitted to a clearing module. This variant embodiment has the advantage, inter alia, that characteristic cost dependencies are used as a trigger for the system. The cost/time parameters can have their reciprocal dependency stabilized for certain instances, e.g. following a first therapy attempt and/or intervention, which makes it possible to initiate the trigger. This has not been possible in the prior art to date.

In another variant embodiment, a storable time-based correlation parameter can be used to define the dependency of the intervention systems linearly and/or exponentially and/or polynomially. The storable time-based correlation parameter may be able to be altered dynamically, in particular, by means of an appropriate module. This variant embodiment has the same advantages, inter alia, as the previous one. In addition, it is thus possible for the coupling of the intervention systems to be adapted by the inventive activation and/or control apparatus, which allows the system to adapt its response as a whole to changed ambient conditions and/or framework parameters. The adaptation may be implemented in self-adaptive and/or dynamic form, for example, by means of appropriate expert modules. Such automated systems are totally unknown in the prior art. This comes particularly from the fact that the correlations in the systems from the prior art cannot be controlled or can be controlled only with difficulty.

In yet another variant embodiment, activation prompts clearing data to be transmitted from the automated intervention systems to a clearing module, which clearing data comprise charging data for the access to services and also user data and which user data comprise information about the user-specific access. By way of example, the clearing module can be used to credit and/or debit the user with services and/or to provide the provider of said services with information in line with the transmitted clearing data, which information can be generated by the clearing module according to stipulated reuse conditions on the basis of the user data. This variant embodiment has the advantage, inter alia, that it allows complete automation to be implemented without any human interaction being necessary. In particular, the user does not need to worry about anything else, but rather the services obtained are charged for and accordingly paid for without his involvement.

In another variant embodiment, the activation and control apparatus has means for encrypted and access-controlled transmission of the activation impulse and/or the activation parameters and/or activation data, where a data token can be generated and transmitted to the relevant intervention system in line with transmitted access request data in order to decrypt the access-controlled activation impulse, the data token respectively comprising data, which comprise at least portions of an appropriate key for the access-controlled encrypted activation impulse, or comprising an access permit for a key for decrypting the activation impulse. By way of example, the data token may be in encrypted and/or electronically signed form. This variant embodiment has the advantage, particularly in the case of decentralized control and activation apparatuses arranged in a network, that the security of the system can be significantly increased without needing to forsake the advantages of network coupling. Quite generally, however, the variant embodiment has the advantage, inter alia, that the apparatus allows a high security standard and a technically stable response during interchange between the systems. As mentioned, the data token may be in encrypted and/or electronically signed form, for example. In particular, the encryption can be performed using public key cryptography, particularly SSL (Secure Sockets Layer) or HTTPS, for example.

At this juncture, it should be stated that the present invention relates not only to the inventive process but also to a system for carrying out this process and to an appropriate computer program product.

Variant embodiments of the present invention are described below with the aid of examples. The examples of the embodiments are illustrated by the following enclosed figures:

FIG. 1 shows a block diagram which schematically shows an activation and trigger apparatus 11 which can be used to implement the invention. Decentralized registering apparatuses 401, 402, 403, 411, 412, 413, 421, 422, 423 use sensors and/or measuring apparatuses to detect appropriate events and use event parameters to transmit them to a first control apparatus 10, a second control apparatus 12 being able to be activated by means of the first control apparatus 10 on the basis of operation-specific activation in line with the transmitted event parameters.

DETAILED DESCRIPTION

Figure 1:
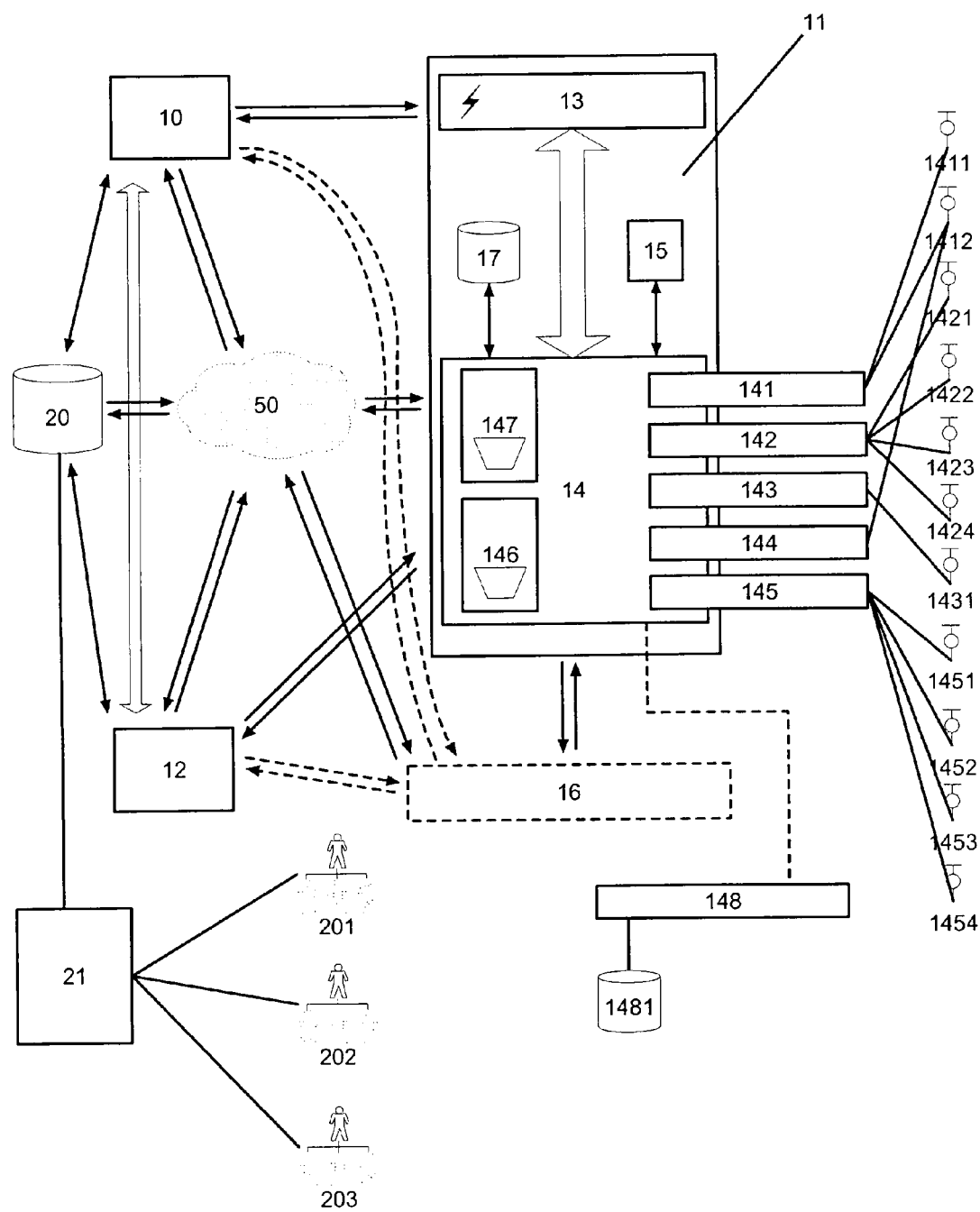
FIG. 1 shows a block diagram which schematically shows an exemplary embodiment of an inventive activation and control apparatus 11 for coupling two reciprocally or complementarily activatable or automated intervention systems 10/12 for coverage events in medical diagnosis and/or therapy processes with a likewise inventive proxy trigger 14.
Figure 2:
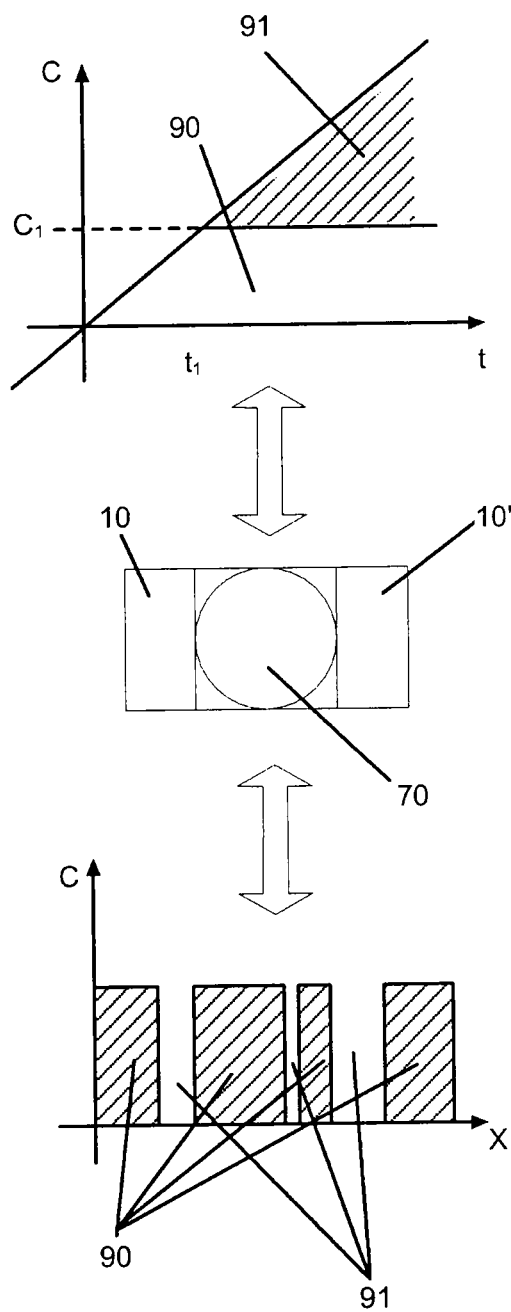
FIG. 2 shows a block diagram which schematically illustrates the example of coverage by first intervention systems 10, 10'. Registered intervention events and/or coverage events from users 201, . . . , 203 of a national intervention system 10' or partially national system or entirely private intervention system 10 are covered by the systems usually only up to a certain damage sum $C_1$ and/or a certain time-based threshold value $t_1$. In other instances, the intervention events are actually allowed only in part 90, while specific other intervention events 91 are excluded entirely or, from the outset, in part, i.e. do not initiate any activation.
Figure 3:
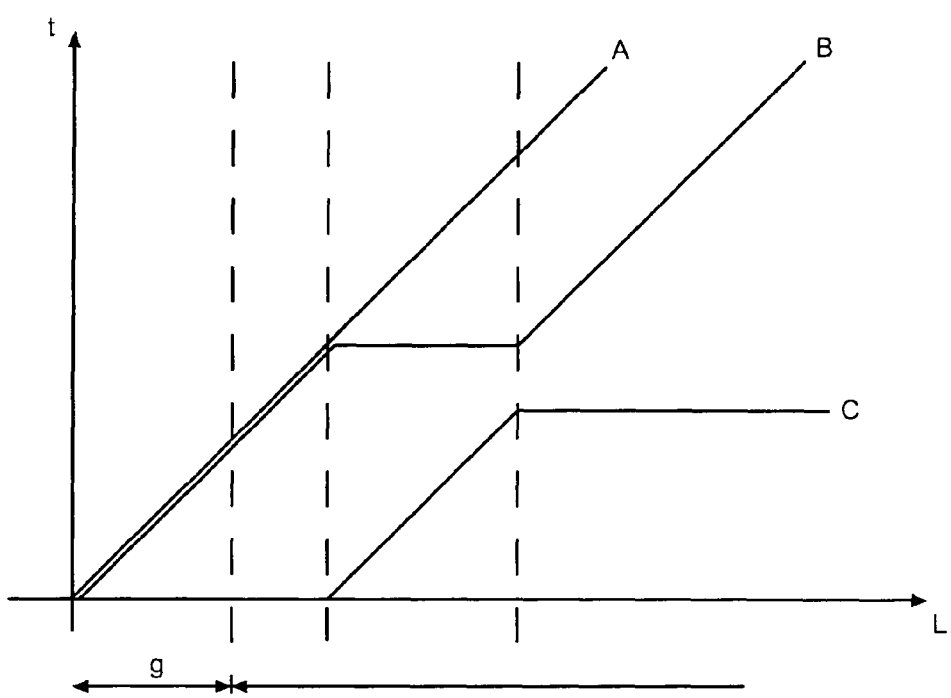
FIG. 3 uses the curve to illustrate an example of a ratio for transmitted event parameters. B shows the interventions for which the first intervention apparatus 10 is responsible and C shows the area covered by the second intervention apparatus 12. In area g, the ratio of transmitted event parameters to the interventions for which settlement has been received from the users 201, . . . , 203 may be greater than 1, for example, while 1 shows the area in which the ratio is less than 1. In the case of cash-value-based apparatuses reference is also made to losses by the first intervention apparatus 10. In the case of cash-value-based systems, reference is also made to what are known as SL (Stop Loss) processes on the basis of the whole of all damage to a technical facility or for the duration of the SL process for cash-value-based intervention systems.

FIG. 1 illustrates an architecture which can be used to implement the invention's authentication. FIG. 1 shows a block diagram which schematically shows an inventive activation and control apparatus 11 for coupling two reciprocally or complementarily activatable automated intervention systems 10/12 for coverage events in medial diagnosis and/or therapy processes. By way of example, the intervention systems 10/12 may comprise cash-value-based intervention systems for medical and/or therapeutic processes. For the special instance of cash-value-based intervention systems, the intervention parameters, i.e. the instances in which at least one of the intervention systems 10/12 should be activated, are frequently subject to country-specific legal regulations, this special instance covering private systems 10 and/or national systems 10' and/or partially national systems. As a borderline case, the intervention systems 10/12 may even comprise health insurance funds and accident prediction systems, such as national facilities for invalid and accident pensions, which would be automatically activated using the activation and control apparatus 11. FIG. 2 schematically shows an example of such coverage by first cash-sum-value-based intervention systems 10/10'. Identical elements are denoted by the same reference numerals or reference symbols in FIGS. 1 and 2. The reference symbol C indicates the cash-sum level of the intervention events in this case and the reference symbol t shows the time axis, for example. Registered intervention events or coverage events 90/91 from users 201, . . . ,203 of a national system 10 or partially national system or entirely private system 10' are covered by these systems usually only up to a certain coverage sum $C_1$ and/or a certain time-based threshold value $t_1$. In other instances, the intervention events are actually allowed only in part 90, while specific other intervention events 91 are excluded entirely or, from the outset, in part. Usually, the manner of operation and the activation of the first intervention systems 10/10' are restricted or controlled by nationally or partially nationally regulated guidelines, such as legal provisions, decrees or other national constraints 70.

As mentioned, however, it is also possible for the intervention systems to be control and alarm apparatuses or systems for direct intervention with the user which are activated upon detection of appropriate events with and/or concerning a user. This can be done by coupled and/or graduated treatment interventions, for example, such as initiation of different metering for appropriate metering apparatuses, e.g. for automated administration of medicaments etc. Equally, intervention systems are possible which are activated, in the sense of alerted, by the activation apparatus, for example (e.g. automated emergency intervention by medically trained personnel or automated initiation of ambulance services etc. etc.). The automated intervention systems 10/12 comprise a multiplicity of associated users 201, . . . ,203. By way of example, the users 201, . . . ,203 can be registered in the form of user-specific data records by a registering apparatus 21 and stored in a memory unit 20 so that they can be accessed. The module 20 may be implemented as a stand alone network module or as part of the activation and control apparatus 11, for example. If it is in the form of a network module 20, it may comprise one or more different physical network interfaces which are also able to support a plurality of different network standards, for example. The physical network interfaces may comprise, by way of example, interfaces to WLAN (Wireless Local Area Network), Bluetooth, GSM (Global System for Mobile Communication), GPRS (Generalized Packet Radio Service), USSD (Unstructured Supplementary Services Data), UMTS (Universal Mobile Telecommunications System) and/or Ethernet or another Wired LAN (Local Area Network) etc. Accordingly, the network 50 may represent various heterogeneous networks, such as a Bluetooth network, e.g. for installation in sheltered localities, a mobile radio network with GSM and/or UMTS etc., a Wireless LAN, e.g. based on IEEE wireless 802.1x, or else a Wired LAN, i.e. a local landline network, particularly also the PSTN (Public Switched Telephone Network) etc. In principle, it can be said that the process and/or system is not tied to one specific network standard, provided that the inventive features are in place, but rather, if it is implemented via a network 50, can be implemented with any LAN. The interfaces may be not only packet-switched interfaces, such as are used directly by network protocols such as Ethernet or TokenRing, but also circuit-switched interfaces, which can be used using protocols such as PPP (Point to Point Protocol), SLIP (Serial Line Internet Protocol) or GPRS (Generalized Packet Radio Service), i.e. which have interfaces, e.g. not a network address like an MAC or DLC address. As mentioned to some extent, the communication can take place via the LAN, for example using specific short messages, e.g. SMS (Short Message Services), EMS (Enhanced Message Services), via a signalling channel, such as USSD (Unstructured Supplementary Services Data) or other techniques, such as MExE (Mobile Execution Environment), GPRS (Generalized Packet Radio Service), WAP (Wireless Application Protocol) or UMTS (Universal Mobile Telecommunications System) or via IEEE wireless 802.1x or another user channel. The intervention apparatuses 10/12 and/or the activation and control apparatus 11 and/or the module 20 and/or the clearing module 16 may even comprise a mobile IP module and/or an IPsec module, for example. The main task of the Mobile IP is to authenticate the at best mobile intervention apparatuses 10/12 and/or activation and control apparatuses 11 and/or module 20 in the IP network and to reroute the IP packets, which have the relevant intervention apparatus 10/12 and/or activation and control apparatus 11 and/or module 20 as destination address, as appropriate. For the further Mobile IP specifications, for example see also IEFT (Internet Engineering Task Force) RFC 2002, IEEE Comm. Vol. 35 No. 5 1997 etc., Mobile IP supports IPv6 and IPv4, in particular. The mobile IP capabilities can preferably be combined with the security mechanisms of an IPsec (IP security protocol) module in order to guarantee secure mobile data management on the public Internet. IPsec (IP security protocol) produces authentication/confidentiality mechanisms on a packet or socket basis between network nodes which both use IPsec. One of the flexibilities of IPsec is particularly that it can be configured on a packet basis but also for individual sockets. IPsec supports IPvx, particularly IPv6 and IPv4. For more detailed IPsec specifications, see Pete Loshin: IP Security Architecture; Morgan Kaufmann Publishers; 11/1999 or A technical guide to IPsec; James S et al.; CRC Press, LLC; 12/2000 etc., for example. Although IPsec has been described in this exemplary embodiment as an example of the use of security protocols at IP level, any other security protocols or mechanisms which are possible, or even omission of security protocols, are conceivable on the basis of the invention.

The automated intervention systems 10/12 are activated by means of activation data from the activation and control apparatus 11. Activation of the intervention systems 10/12 means that they act for a prescribed intervention event. By way of example, this may comprise activation of alarm units and/or monitoring units and/or control units and/or other direct action units. In the case of cash-value-based intervention systems 10/12, this may also include coverage of services required by the user and/or patient by a service provider, such as infirmaries, private doctors, therapists, health facilities etc. etc. The activation and control apparatus 11 comprises a proxy trigger 14. Proxy trigger 14 means that it requires no other trigger modules, and therefore all desired intervention events are triggered using this single trigger 14. Alternatively, the proxy trigger 14 may also be understood to mean an automated detection system and/or detection apparatus which can replace the usually totally different, heterogeneous triggers for detecting intervention events which are known in the prior art. As mentioned, the proxy indicates that it requires no other trigger modules or systems, but rather the proxy trigger registers or triggers all of the relevant intervention events which are not registered by the first stage.

The proxy trigger 13 may comprise first measuring apparatuses and/or registering apparatuses 141. The first measuring apparatuses 141 are used to detect first measurement parameters on the basis of user-specific walking distance and/or a user-specific visual accuracy and/or a user-specific sitting period and to store them in a lookup table 15 in association with the user 201, . . . ,203. The first and/or fourth (mentioned further below) measuring apparatuses 141/144 may comprise at least one eyetracking apparatus 1411 and/or one or more pressure sensors 1412. The pressure sensors are in a form such that the sitting period and/or sitting ability in general and/or walking distance can be registered automatically. Moreover for example, they may be fitted in a chair or seat provided for this purpose or in the ground on an appropriate walking route. The eyetracking apparatus 1411 can be used, for example in combination with pressure sensors or on its own, to allow automatic checking of visual accuracy on the basis of the object viewed by a user 201, . . . ,203. The proxy trigger 14 may comprise, in combination with the first or on its own, second measuring apparatuses and/or registering apparatuses 142. The second measuring apparatuses 142 are used to detect second measurement parameters on the basis of user-specific communication ability and to store them in a lookup table 15 in association with the user 201, . . . ,203. The user-specific communication ability comprises at least aural and/or visual and/or comprehension measurement parameters for the user 201, . . . ,203. The second measuring apparatuses 142 may comprise, by way of example, apparatuses for generating multimedia data 1421 and/or audio output apparatuses 1422 and/or image presentation apparatuses 1423 and touchscreens 1424 and/or appropriate input appliances. The proxy trigger 14 may comprise, in combination with the preceding ones or on its own, third measuring apparatuses and/or registering apparatuses 143. The third measuring apparatuses 143 are used to detect third measurement parameters on the basis of the user-specific ability to drive a motor vehicle and to store them in a lookup table 15 in association with the user 201, . . . ,203. The third measuring apparatuses 143 may comprise means 1431 for bidirectionally accessing appropriate databases with data concerning the health-relating framework parameters for motor vehicle driver licensing. These framework parameters can then be taken as a basis for the measuring apparatuses to automatically check the user-specific ability to drive a motor vehicle. The third measuring apparatuses 143 may additionally comprise means for access-controlled and/or encrypted access to medical and/or national databases with data concerning the vehicle driver licensing for one or more users 201, . . . ,203. This allows secure access to the usually access-controlled databases.

The proxy trigger 14 may, in combination with the preceding ones or on its own, comprise fourth measuring apparatuses and/or registering apparatuses 144. The fourth measuring apparatuses 144 are used to detect fourth measurement parameters on the basis of the user-specific ability to lift oneself or stand independently and to store them in a lookup table 15 in association with the user 201, . . . ,203. The proxy trigger 14 may, in combination with the preceding ones or on its own, comprise fifth measuring apparatuses and/or registering apparatuses 145. The fifth measuring apparatuses 145 are used to detect fifth measurement parameters on the basis of the user-specific ability to write and/or to use a keypad-based input apparatus and to store them in a lockup table 15 in association with the user 201, . . . ,203.

The proxy trigger 14 comprises a filter module 146. The filter module 146 is used to generate appropriate activation parameters on the basis of the measurement parameters in the lookup table 15 and associated, synchronized threshold parameters and to transmit them to the activation and control apparatus 11 if at least one of the measurement parameters exceeds an associated threshold value. The activation and control apparatus also comprises means 13 for generating the activation data on the basis of the activation parameters. At least one of the measuring apparatuses 141, . . . ,145 may additionally comprise a definable time-based threshold value which can be stored in a memory unit 17 in association. The proxy trigger 14 may additionally comprise means for the dynamic user-specific registering of at least one or some of the threshold values, for example. Since every user and his environment (e.g. type of work, workload, social involvement, body-specific characteristics (such as weight, bone structure, muscle proportions etc.), eating habits, body mass index etc.) entail and need to meet greatly differing prerequisites, it may make sense to adapt the threshold values for intervention on a user-specific basis. This cannot be done automatically by the systems in the prior art. The measuring apparatuses 141, . . . ,145 can also adapt the threshold values dynamically directly with the user. For the dynamic registering, the proxy trigger 14 may comprise means for detecting appropriate user-specific parameters. These user-specific parameters can then be taken as a basis for adapting the threshold values dynamically. This is a great advantage over the prior art, since the threshold values are determined there either generally for all users or user groups or, if they are adapted on a user-specific basis, are then stipulated at the time of intervention parameter stipulation, i.e. when the framework parameters for the intervention between the user and the intervention system are stipulated. The inventive apparatus makes it possible to determine the threshold value parameters dynamically, i.e. at the time of the intervention event, for the first time. This means that the framework parameters for intervention are not stipulated, but rather can be defined so as to be able to be altered on the basis of ambient conditions or other user-specific characteristics. This is novel over the systems in the prior art in every respect. For cash-value-based systems, at least one of the threshold values can also be determined on the basis of cash-sum values associated with a service, for example. The proxy trigger 14 may also aggregate data from at least one medical service provider, concerning services for a patient 201, . . . ,203 which are provided on a static basis, using a registering apparatus 12, for example, and stores the data 111 in time-based association with the patient 201, . . . ,203. Medical service providers can quite generally cover service providers in the health and welfare sector, such as infirmaries, rehabilitation clinics, institutions for long-term patients (paraplegics, tetraplegics, physically handicapped, geriatrics etc.). The aforementioned data from services provided for users, in the special case what are known as patient data, may comprise multimedia data, for example, inter alia digital data such as text, graphics, pictures, maps, animations, moving pictures, video, quicktime, sound recordings, programs (software), program-accompanying data and hyperlinks or references to multimedia data. These also include MPx (MP3) or MPEGx (MPEG4 or 7) standards, for example, as defined by the Moving Picture Experts Group. As mentioned, the data or patient data from the service provider may be stored at different locations in different networks 50 or locally so as to be able to be accessed by the proxy trigger 14. The patient data may, in particular, also comprise metadata, which are extracted using a content-based indexing technique, for example. The metadata may comprise, for example, headwords, synonyms, reference to multimedia data (e.g. also hyperlinks) or other patient data, picture and/or sound sequences etc. Such systems are known in many different variations in the prior art. Examples are the U.S. Pat. No. 5,414,644, which describes a three-file indexing technique, or the U.S. Pat. No. 5,210,868, which additionally also stores synonyms as search keywords when indexing the multimedia data and extracting the metadata. As one exemplary embodiment, the metadata may at least in part be produced dynamically (in real time) on the basis of trigger data from the proxy trigger 14. This has the advantage that the metadata always have the appropriate level of currentness and accuracy for the inventive system, for example.

Upon activation, clearing data can be transmitted from the automated intervention systems 10/12 to a clearing module 16, for example. The clearing data may comprise charging data for the access to services and also user data, and the user data may comprise data about the user-specific access. The clearing module 16 can be used to credit and/or debit the user 201, . . . ,203 with services and/or to provide the provider of said services with information in line with the transmitted clearing data, for example. The information can be generated by the clearing module 16, for example, on the basis of the user data according to stipulated reuse conditions.

The proxy trigger 14 may additionally comprise a network module. The network module can be used to access one or more databases of at least one medical or therapeutic service provider. In addition, the proxy trigger 14 in this variant embodiment comprises a second filter module 147 for aggregating historical user data. At least one of the threshold values is then determined using the second filter module 147 on the basis of the aggregated historical data. Historical data are understood to mean data based on services provided for earlier and sometimes completed intervention events. The historical intervention events usefully concern a multiplicity of historical data from events for other users and/or patients in the intervention systems 10/12. As set out further below, when a second threshold value is exceeded by aggregated service data from the users 201, . . . ,203, charging data with charging parameters for crediting cash-sum values to the user and/or patient 201, . . . ,203 and/or medical service provider can be transmitted to a clearing module 16. In particular, the charging data may be based at least on the services provided by the medical service providers.

By way of example, the proxy trigger 14 may comprise means for bidirectional access-controlled access to one or more databases of a medical and/or therapeutic service provider. This can entail additional automation. At the same time, it also allows a significant increase in the security standard. By way of example, the proxy trigger 14 may comprise a supplementary trigger module 148. The supplementary trigger module 148 may comprise a memory unit 1481 for storing definable triggerable illness type data and/or illness status data and/or treatment type data. The supplementary trigger module 148 can be used to filter data concerning services provided in diagnosis and therapy processes on the basis of the illness data types and/or illness status data and/or treatment type data, for example for at least one medical service provider. When one of the illness type data and/or illness status data and/or treatment type data is detected, the charging data with charging parameters for crediting cash-sum values to the user 201, . . . ,203 and/or medical service provider are transmitted to a clearing module 16 in this variant embodiment. For example, the illness type data and/or illness status data may comprise at least data concerning specific types of cancer and/or data concerning the cancer stage of a specific type of cancer. The treatment type data may comprise at least data concerning specific organ transplants, for example. In addition, the treatment type data may comprise at least data concerning specific cardiac surgical intervention. The illness type data may comprise at least data concerning illnesses with the expected long-term dependency of the relevant user 201, . . . ,203, for example. In particular, the supplementary trigger module 148 may comprise means for dynamically registering the long-term dependency of different illness types on the basis of locally stored data from medical service providers based on services provided in diagnosis and therapy processes, for example. On the basis of the long-term dependency, the threshold values for the activation and control apparatus 11 can be dynamically adapted to changed conditions, for example, without the intervention systems 10/12 collapsing. By way of example, the intervention options may change greatly as a result of newly developed technologies or treatment processes. Illnesses which previously required a relatively long stay in an infirmary, for example, may suddenly be able to be treated on an outpatient basis, for example, as a result of new processes etc. etc.

In the case of the stated variant embodiment with cash-value-based intervention systems 10/12, charging data can be generated both by the service providers and/or by the proxy trigger 14 in line with the services obtained. The charging data may comprise charging records (e.g. electronically signed), for example, in similar fashion to CDRs (Call Data Records) in the case of what are known as DURs (DAB/DVB Usage Records). The charging records are transmitted from the proxy trigger 14 and/or the activation and control apparatus 11 to a clearing module 16. The clearing module may also be locally associated with third parties such as a credit card company. The clearing module 16 is used to process the charging data further, or the proxy trigger 14 and/or the activation and control apparatus 11 comprises means for implementing the charging independently. Using a repackaging module, the service-oriented and/or clearing-module-specific charging data and/or patient data can be also be provided with an electronic stamp, an electronic signature or an electronic watermark in optimized fashion. The electronic signature allows the charging data and/or patient data to be associated with a user and/or patient 201, . . . ,203 and/or with a service provider and/or proxy trigger 14 and/or activation and control apparatus 11 (if there are several different ones) at any later time.

LIST OF REFERENCES

10 First intervention system
11 Activation and control apparatus
12 Second intervention system
13 Generator module for activation impulse
14 Proxy trigger
   141 First measuring and/or registering apparatuses
      1411 Eyetracking apparatus
      1412 Pressure sensor
   142 Second measuring and/or registering apparatuses
      1421 Multimedia data apparatus
      1422 Audio output apparatus
      1423 Screen
      1424 Touchscreen
   143 Third measuring and/or registering apparatuses
      1431 Network interface
   144 Fourth measuring and/or registering apparatuses
   145 Fifth measuring and/or registering apparatuses
      1451 Keypad
      1452 Pressure-sensitive input tablet
      1453 Touchscreen
   146 Filter module
   147 Second filter module
   148 Supplementary trigger module
      1481 Memory unit
15 Lookup table
16 Clearing module
20 Memory unit
   201/202 User
21 Registering apparatus/filter apparatus
50 Network

The invention claimed is:

1. An activation and control apparatus for coupling two complementarily activatable automated intervention systems for coverage events in at least one of medical diagnosis and therapy processes, the automated intervention systems being associated with a plurality of users, the automated intervention systems being activated by means of activation data from the activation and control apparatus, the activation and control apparatus comprising:
   a proxy trigger including
      first measuring apparatuses configured to detect first measurement parameters on the basis of at least one of a user-specific walking distance, a user-specific visual accuracy, and a user-specific sitting period, and configured to store the first measurement parameters in a lookup table in association with a user of the plurality of users,
      second measuring apparatuses configured to detect second measurement parameters on the basis of a user-specific communication ability, and to store the second measurement parameters in the lookup table in association with the user, the user-specific communication ability including at least one of aural, visual, and comprehension measurement parameters for the user,
      third measuring apparatuses configured to detect third measurement parameters on the basis of a user-specific ability to drive a motor vehicle, and to store the third measurement parameters in the lookup table in association with the user,
      fourth measuring apparatuses configured to detect fourth measurement parameters on the basis of the user-specific ability to lift oneself or stand independently, and to store the fourth measurement parameters in the lookup table in association with the user, and
      fifth measuring apparatuses configured to detect fifth measurement parameters on the basis of the user-specific ability to at least one of write and use a keypad-based input apparatus, and to store the fifth measurement parameters in the lookup table in association with the user;
   a filter module configured to generate appropriate activation parameters on the basis of the first, second, third, fourth, and fifth measurement parameters in the lookup table and associated synchronized threshold values and to transmit the first, second, third, fourth, and fifth measurement parameters to the activation and control apparatus if at least one of the first, second, third, fourth, and fifth measurement parameters exceeds an associated threshold value, at least one of the threshold values corresponding to cash-sum values associated with a service;
   means for generating the activation data on the basis of the activation parameters; and
   a clearing module configured to automatically obtain and pay for at least one service for the user, without user intervention, in response to one of the two complementarily activatable automated intervention systems being activated by the activation data.

2. The activation and control apparatus according to claim 1, wherein at least one of the first, second, third, fourth, and fifth measuring apparatuses include a definable time-based threshold value which is stored in a memory unit in association with a measurement parameter.

3. The activation and control apparatus according to claim 1, wherein at least one of the first and fourth measuring apparatuses include at least one eyetracking apparatus and one or more pressure sensors.

4. The activation and control apparatus according to claim 1, wherein the second measuring apparatuses include at least one of apparatuses for generating multimedia data, audio output apparatuses, image presentation apparatuses, touchscreens, and appropriate input appliances.

5. The activation and control apparatus according to claim 1, wherein the third measuring apparatuses include means for bidirectionally accessing appropriate databases with data concerning health-related framework parameters for motor vehicle driver licensing.

6. The activation and control apparatus according to claim 5, wherein the third measuring apparatuses additionally include at least one of means for access-controlled and encrypted access to at least one of medical and national databases with data concerning the vehicle driver licensing for one or more users.

7. The activation and control apparatus according to claim 1, wherein the fifth measuring apparatuses include at least one of input apparatuses with keypad-based input elements, pressure-sensitive input tablets, and touchscreens.

8. The activation and control apparatus according to claim 1, wherein activation prompts clearing data to be transmitted from the one of the two complementarily activatable automated intervention systems to the clearing module, the clearing data include charging data for the access to services and user data that include information about user-specific access.

9. The activation and control apparatus according to claim 8, wherein the clearing module is configured to at least one of credit and debit the user with services and to provide a provider of said services with information in line with the transmitted clearing data, the information being generated by the clearing module according to stipulated reuse conditions on the basis of the user data.

10. The activation and control apparatus according to claim 1, wherein the proxy trigger includes means for dynamic user-specific registering of at least some of the threshold values.

11. The activation and control apparatus according to claim 10, wherein the dynamic user-specific registering the proxy trigger includes means for detecting appropriate user-specific parameters, the user-specific parameters being taken as a basis for dynamically adapting the threshold values.

12. The activation and control apparatus according to claim 1, wherein the intervention systems include cash-value-based intervention systems for at least one of medical and therapeutic processes.

13. The activation and control apparatus according to claim 1, wherein the proxy trigger includes a network module that is used by at least one medical or therapeutic service provider to access one or more databases, and includes a second filter module for aggregating historical user data, at least one of the threshold values being determined by means of the second filter module on the basis of the aggregated historical data.

14. The activation and control apparatus according to claim 1, wherein the proxy trigger includes means for bidirectional access-controlled access to one or more databases by at least one of a medical and a therapeutic service provider.

15. The activation and control apparatus according to claim 8, wherein the proxy trigger includes a supplementary trigger module that includes a memory unit for storing at least one of definable triggerable illness type data, illness status data, and treatment type data, the supplementary trigger module being used by at least one medical service provider to filter data concerning services provided in diagnosis and therapy processes on the basis of the at least one of the illness type data, the illness status data, and the treatment type data, and detection of the at least one of the illness type data, the illness status data, and the treatment type data prompting the charging data with charging parameters for crediting cash-sum values to at least one of the user and medical service provider to be transmitted to the clearing module.

16. The activation and control apparatus according to claim 15, wherein the at least one of the illness type data and the illness status data include at least one of data concerning specific types of cancer and data concerning a cancer stage of a specific type of cancer.

17. The activation and control apparatus according to claim 15, wherein the treatment type data include at least data concerning specific organ transplants.

18. The activation and control apparatus according to claim 15, wherein the treatment type data include at least data concerning specific cardiac surgical intervention.

19. The activation and control apparatus according to claim 15, wherein the illness type data include at least data concerning illnesses with expected long-term dependency of the relevant user.

20. The activation and control apparatus according to claim 19, wherein the supplementary trigger module includes means for dynamically registering the long-term dependency of different illness types on the basis of locally stored data from medical service providers based on services provided in diagnosis and therapy processes.

21. An activation and control process for coupling two complementarily activatable automated intervention systems for coverage events in at least one of medical diagnosis and therapy processes, the automated intervention systems being associated with a plurality of users, the automated intervention systems being activated using activation data from an activation and control apparatus, the activation and control process comprising:
  detecting, using first measuring apparatuses of a proxy trigger, first measurement parameters on the basis of at least one of a user-specific walking distance, a user-specific visual accuracy, and a user-specific sitting period, and storing the first measurement parameters in a lookup table in association with a user of the plurality of users;
  detecting, using second measuring apparatuses of the proxy trigger, second measurement parameters on the basis of a user-specific communication ability, and storing the second measurement parameters in the lookup table in association with the user, the user-specific communication ability including at least one of aural, visual, and comprehension measurement parameters for the user;
  detecting, using third measuring apparatuses of the proxy trigger, third measurement parameters on the basis of a user-specific ability to drive a motor vehicle, and storing the third measurement parameters in the lookup table in association with the user;
  detecting, using fourth measuring apparatuses of the proxy trigger, fourth measurement parameters on the basis of the user-specific ability to lift oneself or stand independently, and storing the fourth measurement parameters in the lookup table in association with the user;
  detecting, using fifth measuring apparatuses of the proxy trigger, fifth measurement parameters on the basis of the user-specific ability to at least one of write and use a keypad-based input apparatus, and storing the fifth measurement parameters in the lookup table in association with the user;
  generating, using a filter module of the proxy trigger, appropriate activation parameters on the basis of the first, second, third, fourth, and fifth measurement parameters in the lookup table and associated synchronized threshold values and transmitting the first, second, third, fourth, and fifth measurement parameters to the activation and control apparatus if at least one of the first, second, third, fourth, and fifth measurement parameters exceeds the associated threshold value, at least one of the threshold values corresponding to cash-sum values associated with a service;
  generating, using the activation and control apparatus, the activation data on the basis of the activation parameters; and
  automatically obtaining and paying for, using a clearing module, at least one service for the user, without user intervention, in response to one of the two complementarily activatable automated intervention systems being activated by the activation data.

22. The activation and control process according to claim 21, further comprising: detecting, using at least one of the first, second, third, fourth, and fifth measuring apparatuses, a definable time-based threshold value in association with a measurement parameter.

23. The activation and control process according to claim 21, wherein at least one of the first and fourth measuring apparatuses include at least one eyetracking apparatus and one or more pressure sensors.

24. The activation and control process according to claim 21, wherein the second measuring apparatuses include at least one of means for generating multimedia data, audio output apparatuses, image presentation apparatuses, touchscreens, and appropriate input appliances.

25. The activation and control process according to claim 21, further comprising:
  bidirectionally accessing, using the third measuring apparatuses, databases with data concerning the health-related framework parameters for motor vehicle driver licensing, and
  transmitting appropriate user data to the third measuring apparatuses.

26. The activation and control process according to claim 25, further comprising: accessing, using the third measuring apparatuses, at least one of medical and national databases with data concerning the vehicle driver licensing for one or more users under at least one of access control and encryption.

27. The activation and control process according to claim 21, wherein the fifth measuring apparatuses include at least one of input apparatuses with keypad-based input elements, pressure-sensitive input tablets, and touchscreens.

28. The activation and control process according to claim 21, wherein activation prompts transmitting clearing data from the one of the two complementarily activatable automated intervention systems to the clearing module, the clearing data include charging data for the access to services and user data that include information about user-specific access.

29. The activation and control process according to claim 28, further comprising: at least one of crediting and debiting, using the clearing module, the user with services and providing the provider of said services with information in line with the transmitted clearing data, the information being generated by the clearing module according to stipulated reuse conditions on the basis of the user data.

30. The activation and control process according to claim 21, further comprising: dynamically registering, using the proxy trigger, the threshold values at least to some extent on a user-specific basis.

31. The activation and control process according to claim 30, further comprising: detecting, using the proxy trigger, appropriate user-specific parameters for dynamic registering, on the basis of which user-specific parameters the threshold values are dynamically adapted.

32. The activation and control process according to claim 21, wherein the intervention systems include cash-value-based intervention systems for at least one of medical and therapeutic processes.

33. The activation and control process according to claim 21, further comprising:
using a network module included in the proxy trigger, by at least one medical or therapeutic service provider, to access one or more databases,
aggregating historical user data, using a second filter module, and
determining at least one of the threshold values by means of the second filter module on the basis of the aggregated historical data.

34. The activation and control process according to claim 21, further comprising: using the proxy trigger by at least one of a medical and therapeutic service provider to access one or more databases bi-directionally or under access control.

35. The activation and control process according to claim 28, further comprising:
storing, in a memory unit of a supplementary trigger module of the proxy trigger, at least one of definable triggerable illness type data, illness status data, and treatment type data, and
using the supplementary trigger module by at least one medical service provider to filter data concerning services provided in diagnosis and therapy processes on the basis of the at least one of the illness type data, the illness status data, and the treatment type data,
wherein detection of the at least one of the illness type data, the illness status data, and the treatment type data prompts the charging data with charging parameters for crediting cash-sum values to at least one of the user and medical service provider to be transmitted to the clearing module.

36. The activation and control process according to claim 35, wherein the at least one of the illness type data and the illness status data include at least one of data concerning specific types of cancer and data concerning a cancer stage of a specific type of cancer.

37. The activation and control process according to claim 35, wherein the treatment type data include at least data concerning specific organ transplants.

38. The activation and control process according to claim 35, wherein the treatment type data include at least data concerning specific cardiac surgical intervention.

39. The activation and control process according to claim 35, wherein the illness type data include at least data concerning illness with an expected long-term dependency of the relevant user.

40. The activation and control process according to claim 39, further comprising: dynamically registering, using the supplementary trigger module, the long-term dependency of different illness types on the basis of locally stored data from medical service providers based on services provided in diagnosis and therapy processes.

41. A computer-readable storage medium including computer executable instructions, wherein the instructions, when executed by a computer, cause the computer to perform an activation and control process for coupling two complementarily activatable automated intervention systems for coverage events in at least one of medical diagnosis and therapy processes, the automated intervention systems being associated with a plurality of users, the automated intervention systems being activated using activation data from an activation and control apparatus, the activation and control process comprising:
detecting, using first measuring apparatuses of a proxy trigger, first measurement parameters on the basis of at least one of a user-specific walking distance, a user-specific visual accuracy, and a user-specific sitting period, and storing the first measurement parameters in a lookup table in association with a user of the plurality of users;
detecting, using second measuring apparatuses of the proxy trigger, second measurement parameters on the basis of a user-specific communication ability, and storing the second measurement parameters in the lookup table in association with the user, the user-specific communication ability including at least one of aural, visual, and comprehension measurement parameters for the user;
detecting, using third measuring apparatuses of the proxy trigger, third measurement parameters on the basis of a user-specific ability to drive a motor vehicle, and storing the third measurement parameters in the lookup table in association with the user;
detecting, using fourth measuring apparatuses of the proxy trigger, fourth measurement parameters on the basis of the user-specific ability to lift oneself or stand independently, and storing the fourth measurement parameters in the lookup table in association with the user;
detecting, using fifth measuring apparatuses of the proxy trigger, fifth measurement parameters on the basis of the user-specific ability to at least one of write and use a keypad-based input apparatus, and storing the fifth measurement parameters in the lookup table in association with the user;
generating, using a filter module of the proxy trigger, appropriate activation parameters on the basis of the first, second, third, fourth, and fifth measurement parameters in the lookup table and associated synchronized threshold values and transmitting the first, second, third, fourth, and fifth measurement parameters to the activation and control apparatus if at least one of the first, second, third, fourth, and fifth measurement parameters exceeds the associated threshold value, at least one of the threshold values corresponding to cash-sum values associated with a service;
generating, using the activation and control apparatus, the activation data on the basis of the activation parameters; and
automatically obtaining and paying for, using a clearing module, at least one service for the user, without user intervention, in response to one of the two complementarily activatable automated intervention systems being activated by the activation data.

* * * * *